(12) United States Patent
Kim et al.

(10) Patent No.: US 6,827,219 B2
(45) Date of Patent: Dec. 7, 2004

(54) IMPACTOR WITH COOLED IMPACTION PLATE AND METHOD FOR CLASSIFYING AND COLLECTING AEROSOLS USING THE SAME

(75) Inventors: Sang Soo Kim, Seoul (KR); Byung Uk Lee, Daejon (KR)

(73) Assignee: Korea Advanced Institute of Science and Technology, Daejon (KR)

( * ) Notice: Subject to any disclaimer, the term of this patent is extended or adjusted under 35 U.S.C. 154(b) by 238 days.

(21) Appl. No.: 10/135,727

(22) Filed: May 1, 2002

(65) Prior Publication Data

US 2002/0162773 A1 Nov. 7, 2002

(30) Foreign Application Priority Data

May 2, 2001 (KR) ......................................... 2001-23821

(51) Int. Cl.[7] .............................. B01D 41/08; B07B 7/04
(52) U.S. Cl. ................................ 209/143; 209/3; 95/32; 55/434.2; 55/462
(58) Field of Search ............................ 209/3, 11, 139.1, 209/142, 143, 149; 55/418.1, 431, 434.2, 462; 95/31, 32

(56) References Cited

U.S. PATENT DOCUMENTS 5,435,820 A * 7/1995 Daum et al. ............... 55/434.4
5,809,940 A * 9/1998 James et al. ................ 122/4 D
6,322,603 B1 * 11/2001 Walker ......................... 55/444
6,500,221 B2 * 12/2002 Walker et al. ................ 55/444

OTHER PUBLICATIONS

Derwent Abstract 1998-534682 (Pub: HU 9700032A; Pub: Sep. 1998; Author: Ipacs).*

* cited by examiner

*Primary Examiner*—Donald P. Walsh
*Assistant Examiner*—Joseph Rodriguez
(74) *Attorney, Agent, or Firm*—Morrison & Foerster LLP

(57) ABSTRACT

The present invention discloses an impactor with a cooled impaction plate capable of efficiently separating aerosols by cooling the impaction plate below a temperature of fluid inflowing into the impactor and a method for classifying and collecting the aerosols using the same. The impactor with a cooled impaction plate according to the present invention comprises: an accelerating nozzle for accelerating movement of the aerosols; an impaction plate for changing the flowing direction of the aerosols by means of impacting the aerosols exhausted from the accelerating nozzle, and for collecting the aerosols which are out of the flowing path of the aerosols and have larger inertia than critical value, wherein the impaction plate is installed apart from an outlet of the accelerating nozzle; and cooling means for cooling the impaction plate below a temperature of fluid inflowing into the impactor, wherein the cooling means is fixedly installed at the impaction plate.

10 Claims, 3 Drawing Sheets

IMPACTOR WITH COOLED IMPACTION PLATE AND METHOD FOR CLASSIFYING AND COLLECTING AEROSOLS USING THE SAME

TECHNICAL FIELD

The present invention relates to an inertia impactor for classifying and collecting aerosols in the fields of environmental pollution particle measurement and control, and more particularly to an impactor with a cooled impaction plate capable of efficiently separating aerosols by cooling the impaction plate below a temperature of fluid inflowing into the impactor, and to a method classifying and collecting the aerosols by using the same.

BACKGROUND OF THE INVENTION

Recently, as the environmental pollution becomes an important issue, it is more and more necessary to study and develop an environmental pollution measurement apparatus and an equipment for environment pollution materials research. Of the devices, an impactor is frequently used to measure and control aerosols which are one of the main components causing the atmospheric pollution. Namely, the impactor separates, collects and measures aerosols by using inertia of the aerosol whose size is less than 10 $\mu$m, since it has been developed by the environmental particle researchers in 1970s.

The impactor separates the aerosols flowing along a predetermined path into ones having relatively small inertia and the others having relatively large inertia by suddenly changing the flowing path. Namely, when the flowing path is changed, the aerosols which have small inertia are continuously flowing along the path, however the aerosols which have large inertia are getting out of the flowing path due to their own large inertia. Therefore, the impactor can collects the aerosols which are out of the flowing path.

FIG. 1 shows a cross-sectional view of the conventional impactor which includes an accelerating nozzle 20 with a hole accelerating the movement of the aerosols, thereby enlarging their inertia, and an impaction plate 30 for collecting some aerosols which have relatively large inertia.

When fluid including aerosols inflows toward the impactor by external pressure or internal suction, the fluid is accelerated at the accelerating nozzle 20. The aerosols having inertia larger than a critical value among the accelerated aerosols are adhered to the impaction plate 30, and the aerosols having inertia lower than the critical value are continuously flowing together with the fluid along the path.

In the conventional impactor, the inertia is measured by a Stoke's number that is calculated from the kinetic equation of the aerosols. The Stoke's number is defined as follows:

$$St \text{ (Stoke's number)} = \rho_p C V D^2 / 9 \mu W \qquad (1)$$

where $\rho_p$ represents a density of the aerosols, C denotes a slip correction factor of the aerosols, V denotes an average velocity of fluid passing through the accelerating nozzle 20, D is a diameter of the aerosols, $\mu$ is a viscosity of the fluids, W is a diameter or width of the accelerating nozzle 20.

The Stoke's number defined as above represents the inertia magnitude of the aerosols in the impactor, and a classification performance is presented by the Stoke's number.

In order to effectively classify or separate the aerosols according to the prior art, the impaction plate of the impactor is coated by some coating materials. However, the condition that these coating materials can not be used, happens in several cases.

For example, (1) when the aerosols generated in high temperature are sampled, the coating materials become unstable in high temperature, therefore the coating materials can not function properly because the coating materials have liquidity to fall down or vaporized, (2) when the bio-aerosols are sampled by using the impactor with coating materials, it is difficult to analyze the bio-aerosols precisely because the bio-aerosols are contaminated with coating materials.

At those situations in which the coating materials can not be used, the impactor classification efficiency dramatically decrease.

Consequently, because of the condition that the coating materials cannot be used in an impactor, a new impactor having higher classification efficiency without using coating materials is required.

SUMMARY OF THE INVENTION

It is an object of the present invention to provide an impactor with a cooled impaction plate which makes the classification efficiency high without using coating materials by using condensational phenomena and thermophoresis phenomena which represent the kinetic characteristics of the aerosols, and a method classifying and collecting the aerosols using the same.

In order to achieve the object of the present invention, the impactor with a cooled impaction plate is designed, which comprises: an accelerating nozzle for accelerating movement of the aerosols; an impaction plate for changing the flowing direction of the aerosols by means of impacting the aerosols exhausted from the accelerating nozzle, and for collecting the aerosols which are out of the flowing path of the aerosols and have larger inertia than critical value, wherein the impaction plate is installed apart from an outlet of the accelerating nozzle; and cooling means for cooling the impaction plate below a temperature of fluid inflowing into the impactor, wherein the cooling means is fixedly installed at the impaction plate.

In order to achieve the object, the method classifying and collecting aerosols in atmosphere by using an impactor with a cooled impaction plate, comprises the steps of: cooling an impaction plate below a temperature of fluid inflowing into the impactor; exhausting the aerosols from an accelerating nozzle into the impaction plate which is installed apart from an outlet of the accelerating nozzle; changing the flowing direction of the aerosols by means of impacting the aerosols exhausted from the accelerating nozzle; and collecting the aerosols which are out of the flowing path of the aerosols and have larger inertia than critical value.

Preferably, the cooling means is a thermoelectric device fixed at the impaction plate.

More preferably, the thermoelectric device is fixed at the opposite side of an aerosol impacting surface of the impaction plate 30.

Also, the cooling means maintains the temperature of the impaction plate 30 within 0° c.~–5° c.

Preferably, a diameter of an inlet of the accelerating nozzle 20 is larger than a diameter of an outlet 21 of the accelerating nozzle 20.

BRIEF DESCRIPTION OF THE DRAWINGS

The above object and other advantages of the present invention will become more apparent by describing in detail preferred embodiments thereof with reference to the attached drawings in which.

DETAILED DESCRIPTION

The preferable embodiments of the present invention will now be described in details with reference to attached drawings.

Figure 1:
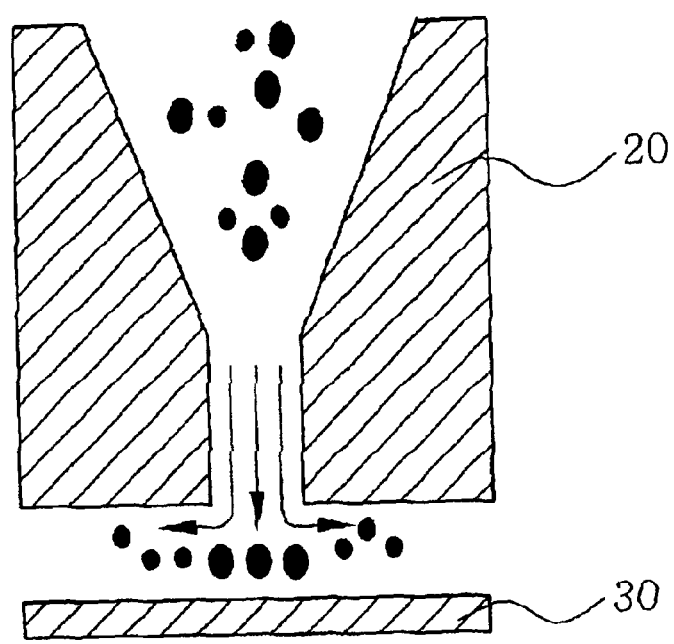
FIG. 1 shows a cross-sectional view of the conventional impactor.
Figure 2:
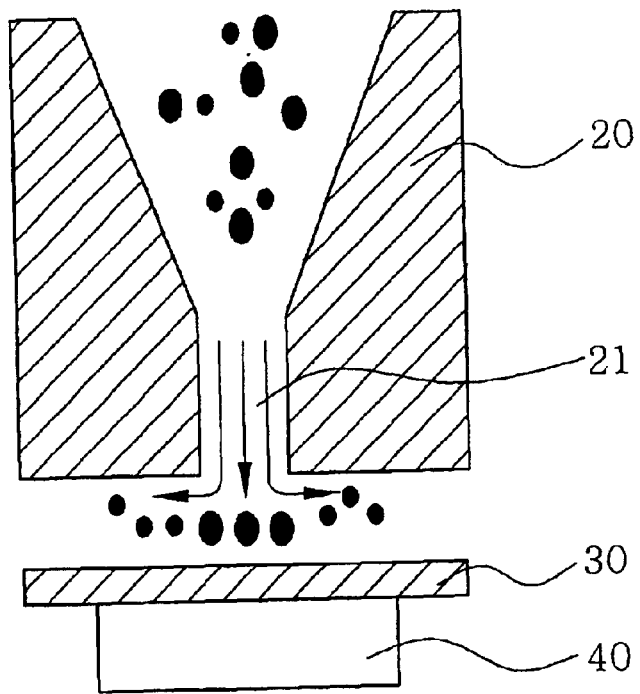
FIG. 2 shows a schematic diagram of the impactor with a cooled impaction plate according to the present invention.
Figure 3:
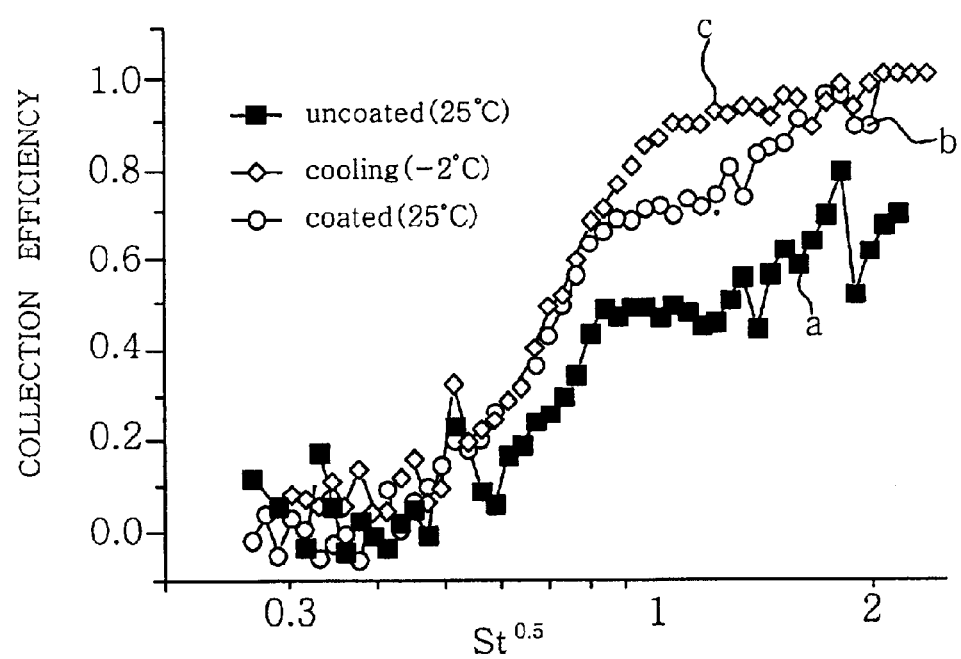
FIG. 3 shows graphs illustrating collection efficiency of the impactor of the present invention by comparison against that of the conventional impactor.

FIG. 2 shows a schematic diagram of the impactor with a cooled impaction plate according to the present invention, which comprises an accelerating nozzle 20 for accelerating movement or velocity of the aerosols; an impaction plate 30 for changing the flowing direction of the aerosols by means of impacting the aerosols exhausted from the accelerating nozzle 20, and for collecting the aerosols which are out of the flowing path of the aerosols and have larger inertia than critical value, wherein the impaction plate 30 is installed apart from an outlet 21 of the accelerating nozzle 20; and a cooling means 40 for cooling the impaction plate 30 below a temperature of fluid inflowing into the impactor, fixed at the impaction plate 30.

Here, the impactor according to the present invention causes a result with high efficiency when the cooling means cools the impaction plate and maintains its temperature below 20° C.~30° C. from the temperature of the fluid inflowing into the impactor.

In the present embodiment, the cooling means is a thermoelectric device as a kind of semiconductor materials. The one surface of the thermoelectric device 40 becomes cold about 0° c.~−5° c., which is attached to the back surface of the impaction plate 30, and the other surface of the thermoelectric device 40 becomes hot when the direct current is supplied to the thermoelectric device 40. As the attached surface of the thermoelectric device 40 becomes cold, the heat of the impaction plate 30 begins to be transferred to the thermoelectric device 40 and the impaction plate 30 is cooled. According to the present invention, the impactor can perform high collection efficiency without coating materials on the cooled impaction plate 30. The above result can be confirmed through the testing result diagram of the FIG. 3.

FIG. 3 shows graphs illustrating collection efficiency of the impactor of the present invention by comparison against that of the conventional impactor.

In order to test the impactor, flyash particles are used as the aerosols and the Reynolds number of the impactor system is maintained about 3300 and is defined as follows:

$$Re \text{ (Reynolds number)}=\rho VW/\mu \qquad (2)$$

where, ρ represents a density of the fluids, V denotes an average velocity of fluid passing through the accelerating nozzle 20, $\mu$ is a viscosity of the fluids, and W is a diameter or width of the accelerating nozzle.

As shown in FIG. 3, a-line represents the testing result of the conventional impactor without the coating materials, c-line represents the testing result of the conventional impactor with coating the impaction plate, and b-line represents the testing result of the impactor according to the present invention without the coating materials.

FIG. 3 are understood that the collection efficiency of the impactor is not high enough for proper particle classification in the high Stoke's number area when the conventional impactor is not coated with coating materials. However, when the impaction plate 30 in FIG. 2 is cooled, the collection efficiency of the impactor becomes higher in the high Stoke's number area. It is shown that the performance of the impactor with the cooled plate is similar to that of the coated plate impactor in FIG. 3.

This phenomenon can be explained by the increase of the adhesion effects by condensation on the cooled impaction plate and thermophoresis. The first reason means that the relative humidity becomes over 100% near the cooled impaction plate, therefore condensation occurs and condensed water plays a role like coating materials. Thermophoresis means that the particles are forced toward the low temperature region when the temperature gradient are formed at the environments. In the present invention, the force is supplied to the aerosols toward the cooled impaction plate 30. As a result, the collection efficiency becomes high.

As described above, the advantages offered by the impactor of the present invention are mainly that the impactor has a high efficiency without the coating materials on the impaction plate. Therefore, the impactor with a cooled impaction plate never have the disadvantages like the coating materials are flowing down and evaporating, or causing contamination, etc. Moreover, the cooling device can be easily adaptable to the impactor regardless of the impactor's size and the cost of the cooling device is not expensive. Consequently, the present invention can be widely applied to the field of the environmental pollution particle measurement, bio-aerosol measurement, and control of aerosols for manufacturing the materials.

Although the preferred embodiment shows thermoelectric device to cool the impaction plate 30, all kinds of cooling devices can be adopted to the present invention, which have no effect on the result. Refrigerant system is also a good embodiment.

While the present invention has been particularly shown and described with reference to particular embodiment thereof, it will be understood by those skilled in the art that various changes in form and details may be effected therein without departing from the spirit and scope of the invention as defined by the appended claims.

What is claimed is:

1. An impactor with a cooled impaction plate for classifying and collecting aerosols in atmosphere, comprising:

an accelerating nozzle for accelerating movement of the aerosols;

an impaction plate for changing the flowing direction of the aerosols by impacting the aerosols exhausted from the accelerating nozzle, and for collecting the aerosols which are outside a flowing path of a fluid including the aerosols, wherein the impaction plate is installed apart from an outlet of the accelerating nozzle; and cooling means for cooling the impaction plate below a temperature of the fluid inflowing into the impactor, wherein the cooling means is fixedly installed at the impaction plate.

2. The impactor according to claim 1, wherein the cooling means is a thermoelectric device.

3. The impactor according to claim 2, wherein the thermoelectric device is fixed at the opposite side of an aerosol impacting surface of the impaction plate.

4. The impactor according to claim 1, wherein the cooling means maintains the impaction plate temperature within 0° C.~−5° C.

5. The impactor according to claim 1, wherein the cooling means cools the impaction plate temperature below 20° C.~30° C. from the temperature of the fluid inflowing the impactor.

6. A method classifying and collecting aerosols in atmosphere by using an impactor with a cooled impaction plate, comprising the steps of:

cooling an impaction plate below a temperature of a fluid inflowing into the impactor;

exhausting the aerosols from an accelerating nozzle into the impaction plate which is installed apart from an outlet of the accelerating nozzle;

changing the flowing direction of the aerosols by impacting the aerosols exhausted from the accelerating nozzle; and collecting the aerosols which are outside a flowing path of the fluid including the aerosols.

7. The method according to claim 6, wherein the temperature range of the cooled impaction plate is within 0° C.~−5° C.

8. The method according to claim 6, wherein the temperature of the impaction plate is lower 20° C.~30° C. than the temperature of the fluid inflowing into the impactor.

9. The impactor of claim 1, wherein the aerosols have an inertia greater than a critical value such that the aerosols are adhered to the impaction plate.

10. An impactor with a cooled impaction plate for classifying and collecting aerosols in atmosphere, comprising:

an accelerating nozzle for accelerating movement of the aerosols;

an impaction plate for changing the flowing direction of the aerosols by impacting the aerosols exhausted from the accelerating nozzle, and for collecting the aerosols which are outside a flowing path of a fluid including the aerosols, wherein the impaction plate is installed apart from an outlet of the accelerating nozzle; and a device that cools the impaction plate below a temperature of the fluid inflowing into the impactor, wherein the device is fixedly installed at the impaction plate.

* * * * *